(12) United States Patent
Garcia-Perez et al.

(10) Patent No.: US 10,760,004 B2
(45) Date of Patent: Sep. 1, 2020

(54) METHOD FOR RECYCLING PYROLYSIS TAIL GAS THROUGH CONVERSION INTO FORMIC ACID

(71) Applicants: TerraPower, LLC, Bellevue, WA (US); Washington State University, Pullman, WA (US)

(72) Inventors: Manuel Garcia-Perez, Pullman, WA (US); Joshua C. Walter, Kirkland, WA (US)

(73) Assignees: TerraPower, LLC, Bellevue, WA (US); Washington State University, Pullman, WA (US)

( * ) Notice: Subject to any disclaimer, the term of this patent is extended or adjusted under 35 U.S.C. 154(b) by 128 days.

(21) Appl. No.: 15/935,654

(22) Filed: Mar. 26, 2018

(65) Prior Publication Data

US 2018/0273846 A1 Sep. 27, 2018

Related U.S. Application Data

(60) Provisional application No. 62/476,264, filed on Mar. 24, 2017.

(51) Int. Cl.
*C10B 57/08* (2006.01)
*C07C 51/00* (2006.01)
(Continued)

(52) U.S. Cl.
CPC ............... *C10B 57/18* (2013.01); *C01B 3/48* (2013.01); *C07C 51/00* (2013.01); *C07C 51/15* (2013.01);
(Continued)

(58) Field of Classification Search
CPC ......... C10B 57/18; C10B 57/06; C10B 53/04; C07C 51/00; C01B 3/48
See application file for complete search history.

(56) References Cited

U.S. PATENT DOCUMENTS 3,115,394 A 12/1963 Gorin
3,890,908 A 6/1975 von Klenck et al.
(Continued)

FOREIGN PATENT DOCUMENTS

CA 2696910 9/2011
CA 2956521 A1 2/2016
(Continued)

OTHER PUBLICATIONS

CN105925317A_English Translation (Year: 2016).*
(Continued)

*Primary Examiner* — Youngsul Jeong

(57) ABSTRACT

This disclosure describes systems and methods for using pyrolysis tail gas as the source for additional hydrogen to be used in the pyrolysis reaction. Tail gas is separated from the pyrolysis products and a portion of the tail gas is converted into formic acid (HCOOH). The formic acid is then injected into the pyrolysis reactor where it becomes the donor of two monohydrogen atoms and is ultimately converted into $CO_2$ under reaction conditions. In this fashion, a closed loop pyrolysis hydrogen donor system may be created utilizing a generally non-toxic intermediary derived from the pyrolysis reaction products. This disclosure also describes using a ruthenium catalyst supported on particles of activated carbon to improve the yield of pyrolysis reactions.

17 Claims, 5 Drawing Sheets

(51) Int. Cl.
| | |
|---|---|
| *C01B 3/48* | (2006.01) |
| *C10B 53/04* | (2006.01) |
| *C10G 1/02* | (2006.01) |
| *C10B 57/18* | (2006.01) |
| *C10B 57/06* | (2006.01) |
| *C10K 3/00* | (2006.01) |
| *C07C 51/15* | (2006.01) |
| *C10K 3/04* | (2006.01) |

(52) U.S. Cl.
CPC .............. *C10B 53/04* (2013.01); *C10B 57/06* (2013.01); *C10G 1/02* (2013.01); *C10K 3/00* (2013.01); *C10K 3/04* (2013.01); *C01B 2203/0222* (2013.01); *C01B 2203/0283* (2013.01); *C01B 2203/06* (2013.01)

(56) References Cited

U.S. PATENT DOCUMENTS

| | | |
|---|---|---|
| 4,138,442 A | 2/1979 | Chang et al. |
| 4,358,344 A | 11/1982 | Sass |
| 4,692,239 A * | 9/1987 | Friedman ............... C10G 1/006 208/430 |
| 5,344,848 A | 9/1994 | Steinberg et al. |
| 5,386,055 A | 1/1995 | Lee et al. |
| 6,783,877 B2 | 8/2004 | Shimazu et al. |
| 7,569,204 B2 | 8/2009 | Leveson |
| 8,579,996 B2 | 11/2013 | Humphreys |
| 8,771,387 B2 | 7/2014 | Simmons et al. |
| 8,647,401 B2 | 11/2014 | Self et al. |
| 9,068,131 B2 | 6/2015 | Ginestra |
| 9,376,639 B2 | 6/2016 | Walter |
| 10,144,874 B2 | 12/2018 | Walter |
| 2002/0031690 A1 | 3/2002 | Shimazu et al. |
| 2002/0048545 A1 | 4/2002 | Lewis |
| 2002/0155062 A1 | 10/2002 | Lightner |
| 2004/0232046 A1 | 11/2004 | Tanaka |
| 2006/0280669 A1 | 12/2006 | Jones |
| 2007/0270513 A1 | 11/2007 | Leveson |
| 2007/0286797 A1 | 12/2007 | Behrens et al. |
| 2008/0040975 A1 | 2/2008 | Calderon |
| 2008/0099377 A1 | 5/2008 | He et al. |
| 2008/0155899 A1 | 7/2008 | Ramamurthy |
| 2009/0077888 A1 | 3/2009 | Zander et al. |
| 2009/0155434 A1 | 6/2009 | Brunner |
| 2009/0206007 A1 | 8/2009 | Allam |
| 2010/0043445 A1 | 2/2010 | Coronella |
| 2010/0056767 A1 | 3/2010 | Gunning |
| 2010/0319255 A1 | 12/2010 | Struble |
| 2011/0000825 A1 | 1/2011 | McGrady |
| 2011/0179799 A1 | 7/2011 | Allam |
| 2011/0180262 A1 | 7/2011 | O'Dowd |
| 2011/0289843 A1 | 12/2011 | Jorgenson |
| 2012/0053378 A1 | 3/2012 | O'Rear |
| 2012/0172622 A1* | 7/2012 | Kocal ..................... C07C 51/00 562/409 |
| 2012/0181217 A1 | 7/2012 | Choi |
| 2013/0025190 A1 | 1/2013 | Cheiky |
| 2013/0199195 A1 | 8/2013 | Allam |
| 2014/0275668 A1 | 9/2014 | Walter |
| 2014/0275678 A1 | 9/2014 | Walter |
| 2015/0141699 A1* | 5/2015 | Barger ................. C07C 45/505 568/312 |
| 2016/0160124 A1 | 6/2016 | Strimling |
| 2016/0272903 A1 | 9/2016 | Walter |
| 2018/0291275 A1 | 10/2018 | Goodrich |
| 2019/0153325 A1 | 5/2019 | Garcia-Perez |

FOREIGN PATENT DOCUMENTS

| | | | |
|---|---|---|---|
| CN | 1320267 | 10/2001 | |
| CN | 1420155 | 5/2003 | |
| CN | 1410511 | 3/2005 | |
| CN | 2906230 | 5/2007 | |
| CN | 101100621 | 1/2008 | |
| CN | 101284984 | 10/2008 | |
| CN | 101323793 | 12/2011 | |
| CN | 102395709 | 3/2012 | |
| CN | 102460039 | 5/2012 | |
| CN | 102876349 | 1/2013 | |
| CN | 105925317 | 9/2016 | |
| CN | 105925317 A * | 9/2016 | ............... C01J 3/60 |
| FR | 973678 | 2/1951 | |
| JP | 52-068107 | 6/1977 | |
| JP | 55-60588 | 5/1980 | |
| JP | 2000273472 | 10/2000 | |
| JP | 2001115174 | 4/2001 | |
| JP | 2001181651 | 7/2001 | |
| JP | 2006-104261 | 4/2006 | |
| JP | 2010-529286 | 6/2007 | |
| JP | 2010-121049 | 6/2010 | |
| JP | 2011088964 | 5/2011 | |
| WO | WO 8100855 | 4/1981 | |
| WO | WO 2009-015409 | 2/2009 | |
| WO | WO 2012092644 | 7/2012 | |
| WO | WO 2012154270 | 11/2012 | |
| WO | WO 2014152645 | 3/2014 | |
| WO | 2016043651 A1 | 3/2016 | |
| WO | 2017023985 A1 | 2/2017 | |

OTHER PUBLICATIONS

Chornet et at, Biomass Liquefaction: An Overview, 1985 Elsevier Applied Science Publishers Ltd, pp. 967-1002.

Demirbas et al., "An Overview of Biomass Pyrolysis", Energy Sources, vol. 24, No. 3, 2002, pp. 471-482.

European Supplementary Search Report for EP14768189 dated Nov. 3, 2016.

European Supplementary Search Report for EP14769519 dated Nov. 2, 2016.

Evans et al., Renewable Hydrogen Production by Catalytic Steam Reforming of Peanut shells Pyrolysis Products, Fuel Chemistry Division Preprints, vol. 47, No. 2, Feb. 20, 1975.

PCT International Preliminary no Patentability in International Application PCT/US2018/027110, dated Oct. 24, 2019, 15 pages.

PCT International Preliminary Report on Patentability in International Application PCT/US2018/024289, dated Oct. 3, 2019, 15 pages.

Turbosystems Engineering Inc., Overview of Supercritical Water Oxidation (SCWO), http://www.turbosynthesis.com/summitresearch/sumscw1.htm ,copyright 2002 Turbosystems Engineering Inc.

Wang et al., Production of Hydrogen from Biomass by Catalytic Steam Reforming of Fast Pyrolysis Oils, Energy & Fuels 12, pp. 19-24, 1998.

Xu et al., The Role of Supercritical Water in Pyrolysis of Carbonaceous Compounds, Energy Fuels, 2013, 27(6), pp. 3148-3153, May 29, 2013.

PCT International Search Report and Written Opinion in International Application PCTUS2014/027530, dated Aug. 8, 2014, 7 pgs.

PCT International Preliminary Report on Patentability in International Application PCTUS2014/027530, dated Sep. 15, 2015, 5 pgs.

PCT International Search Report and Written Opinion in International Application PCTUS2014/027572, dated Aug. 21, 2014, 9 pgs.

PCT International Preliminary Report on Patentability in International Application PCTUS2014/027572, dated Sep. 15, 2015, 7 pgs.

International Search Report and Written Opinion of PCT/US2018/027110 dated Aug. 29, 2018.

Kortlever et al., "Electrochemical CO2 reduction to formic acid on a Pd-based formic acid oxidation catalyst",Catalysis Today. 244, 2015, 58-62.

Kortlever R, Peters I, Koper S, Koper MTM: electrochemical CO2 Reduction to Formic acid at Low Overpotential and with High Faradaic Efficiency on Carbon-Supported Bimetallic Pd-Pt Nanoparticles. ACS Catal., 2015, 5 (7) , pp. 3916-3923.

Hojniak SD, Silverwood IP, Khan AL, Vankelecom IFJ, Dehaen W, Kazarian SG, Binnemans K: Highly Selective Separation of Carbon Dioxide from Nitrogen and Methane by Nirtile/Glycol-

(56) References Cited

OTHER PUBLICATIONS

Difunctionalized Ionic Liquid in Supported ionic Liquid membranes (SILMS). J. Phys. Chem. B, 2014, 118 (26) 7440-7449.
Kapoor A, Yang RT: Kinetic separation of methane-carbon dioxide mixture by absorption on molecular sieve carbon. chemical Engineering Science. vol. 44, 8, 1989, 1723-1733.
Sircar S: Separation of Methane and Carbon Dioxide Gas Mixture by Pressure Swing Adsorption. Separation Science and Technology, vol. 23, 1988, 6-7.
Songolzedeh M, Soleimani M, Ravanchi MT, Songolzadeh R: Carbon Diozide Separation from flue Gases: A tchnological review Emphasizing Reduction in Greenhouse Gas Emissions. The Scientific World Journal, 2014.
Fouga et al., Studies on Nuclear Hydrogen Production by Steam Coal gasification in Argentina, Jul. 17-19, 2017.
International Search Report and Written Opinion of PCT/US2018/024289 dated Jun. 8, 2018.
Moret et al., Direct Synthesis of formic acid from carbon dioxide by hydrogenation in acid media. Nature Communications 5, 2014.

\* cited by examiner

METHOD FOR RECYCLING PYROLYSIS TAIL GAS THROUGH CONVERSION INTO FORMIC ACID

CROSS REFERENCE TO RELATED APPLICATIONS

The present application claims the benefit of U.S. Provisional Patent Application No. 62/476,264, titled "Method and System for Recycling Pyrolysis Tail Gas through Conversion into Formic Acid", filed Mar. 24, 2017, which application is hereby incorporated by reference herein.

INTRODUCTION

Pyrolysis refers to a thermochemical decomposition of organic material at elevated temperatures in the absence of oxygen. Pyrolysis of coal and other biomass feedstocks has been used to generate hydrocarbon products. By providing additional hydrogen during pyrolysis, it is possible to obtain higher value hydrocarbon products than would otherwise be produced. For example, to make 'lighter' oils from coal pyrolysis, hydrogen needs to be available in monoatomic form (versus the diatomic H2 molecule) so that it is capable of being transferred to pyrolysis radicals created via thermal pyrolysis.

Prior approaches utilize tertralin (a hydrogenated form of naphthalene) to supply additional hydrogen during pyrolysis. The tetralin is mixed in coal at high amounts (at least one part tetralin to one part coal, by mass). The dehydrogenated tetralin (naphthalene) typically is recycled and re-hydrogenated. This process is costly and is a barrier to coal liquefaction's commercial success. Tetralin and naphthalene also have toxicology issues to humans and the environment.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Before the pyrolysis methods and systems are disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting. It must be noted that, as used in this specification, the singular forms "a," "an," and "the" include plural referents unless the context clearly dictates otherwise. Thus, for example, reference to "a lithium hydroxide" is not to be taken as quantitative or source limiting, reference to "a step" may include multiple steps, reference to "producing" or "products" of a reaction should not be taken to be all of the products of a reaction, and reference to "reacting" may include reference to one or more of such reaction steps. As such, the step of reacting can include multiple or repeated reaction of similar materials to produce identified reaction products.

This disclosure describes systems and methods for using pyrolysis tail gas as the source for the additional hydrogen to be used in the pyrolysis reaction. The tail gas is separated from the pyrolysis products and a portion of the tail gas is converted into formic acid (HCOOH). The formic acid is then injected into the pyrolysis reaction where it becomes the donor of two monohydrogen atoms and is ultimately converted into $CO_2$ under reaction conditions. In this fashion, a closed loop pyrolysis hydrogen donor system may be created utilizing a generally non-toxic intermediate derived from the pyrolysis reaction products.

Figure 1:
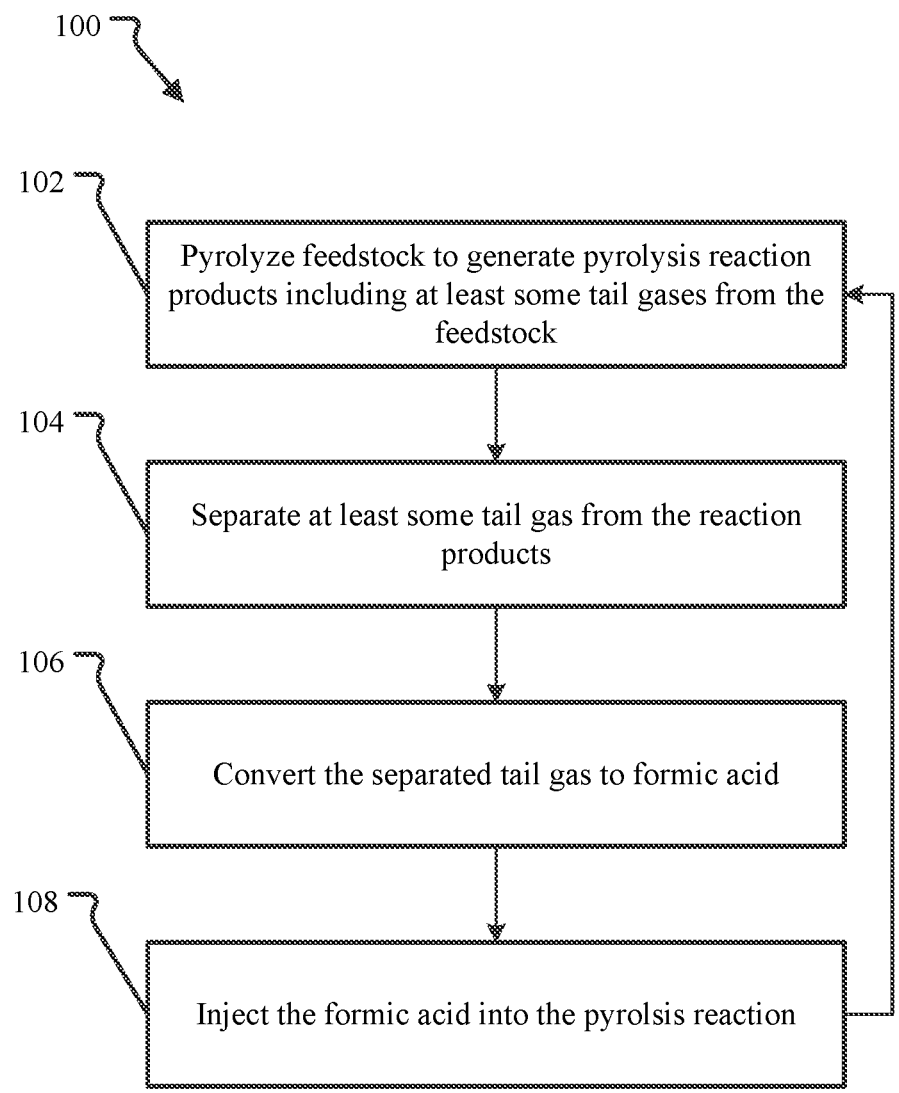
FIG. 1 illustrates, at a high-level, a simplified embodiment of a pyrolysis method that generates donor hydrogen from tail gas of the pyrolysis reaction.

FIG. 1 illustrates, at a high-level, a simplified embodiment of a pyrolysis method that generates donor hydrogen from tail gas of the pyrolysis reaction. In the method 100 shown, a carbonaceous feedstock material is pyrolyzed to obtain pyrolysis reaction products in a pyrolysis operation 102. The pyrolysis may be performed at any suitable temperature and pressure. While different combinations of feedstock and reaction conditions (e.g., temperature, pressure, atmosphere, etc.) will affect the spectrum and relative amounts of reaction products generated, some amount of light hydrocarbon gases such as methane, ethane, propane, butane and related isomers (referred to as $C_1$-$C_4$ gases or, simply, tail gas) will be generated. Depending on the feedstock and pyrolysis conditions, tail gas may include any number and relative amounts of component hydrocarbon gases that are gases at room temperature and pressure.

The feedstock material may include any carbonaceous material known in the art. For example, the feedstock material may include, but is not limited to, coal, biomass, mixed-source biomaterial, peat, tar, plastic, refuse, and landfill waste. For example, in the case of coal, the feedstock may include, but is not limited to, bituminous coal, sub-bituminous coal, lignite, anthracite and the like. By way of another example, in the case of biomass, the feedstock may include a wood material, such as, but not limited to, softwoods or hardwoods. In the detailed embodiments discussed below the feedstock will be presented as coal but the reader will understand that any feedstock may be used and that the system and methods are not limited to coal embodiments.

In the method 100, some fraction of the tail gas is separated from the reaction products in a separation operation 104. The separation operation 104 may separate one or more specific species of gas, such as only methane (as described below with reference to FIG. 2), a combination of methane and ethane, a combination of methane, ethane, and propane, or a combination of propane and ethane, from the other components of the tail gas. Any suitable method for separating the desired gas or gases from the reaction products may be used. For example, in an embodiment, supercritical carbon dioxide ($sCO_2$) may be used as a solvent to remove reaction products from the pyrolyzed feedstock. The sCO2 is then transferred to a collection system where the temperature and/or pressure of the sCO$_2$ may then be reduced, at once or in steps, to generate CO$_2$ gas and reaction products. Depending on the final temperature and pressure, some of the specific components (e.g., methane, butane) in the reaction products will remain as gas while others (e.g., decane) will condense out as liquids, semi-solids, or solids depending on their chemistry. The separated gas fraction may then be diverted and collected for later use. Other separation methods are also possible, including, for example, simply passing a stream of the atmosphere from the reaction chamber through a scrubber to separate the tail gas.

A portion of the separated tail gas is then converted to formic acid in a formic acid generation operation 106. The formic acid generation may include multiple intermediate processes. For example, as described in greater detail below with reference to FIG. 2, the formic acid may be generated by dry reforming methane into carbon monoxide and hydrogen, then performing the water shift reaction to obtain carbon dioxide and hydrogen, and finally, reacting the carbon dioxide and hydrogen under the appropriate conditions to generate formic acid. Each of these reactions is known in the art and any suitable methods for performing these reactions may be used. For example, the process for formic acid production by hydrogenation of CO$_2$ at low temperatures has been extensively studied in the literature (See, for example, Jessop P G, Ikariya T, Noyari R: Homogeneous catalytic hydrogenation of supercritical carbon dioxide. Nature, 1994, 368, 231-233; Jessop P G, Hsiao Y, Ikariya T, Noyori R: Homogeneous Catalysis in Supercritical Fluids: Hydrogenation of Supercritical Carbon dioxide to form formic acid, alkyl formats, and formamides. J. Am. Chem. Soc. 1996, 118, 344-355; Zhang S, Hu S, Song J, Li W, Yang G, Han B: Hydrogenation of CO2 to Formic acid Promoted by a Diamine-Functionalized Ion Liquid. ChemSusChem, 2009, 2, 234-238; Moret S, Dyson P J, Laurenczy G: Direct Synthesis of formic acid from carbon dioxide by hydrogenation in acid media. Nature Communications 5, 2014; Federsel C, Jackstell R, Beller M: State of the Art Catalysts for Hydrogenation of Carbon Dioxide. Angewandte Chemie. 2010, 49, 6254-6257; and Hutschka F, Dedieu A, Eichberger M, Fornika R, Leitner W: Mechanistic Aspects of the Rhodium Catalyzed Hydrogenation of CO2 to formic acid—A theoretical and kinetic study. J. Am. Chem. Soc. 1997, 119, 4432-4443 all of which are incorporated herein by reference for their teachings of formic acid generation from carbon dioxide and hydrogen).

Alternative routes of synthesizing formic acid from tail gas are also possible. For example, dry reforming of light alkanes with CO$_2$ to generate syngas (H$_2$ and CO) has been investigated using PtNi/CeO$_2$ bimetallic catalysis and dry reforming of ethane on tri-metallic perovskites has been shown to generate syngas.

Some or all of the generated formic acid is then used in a subsequent pyrolysis reaction to provide donor hydrogen in an injection operation 108. In the injection operation 108, the formic acid is delivered into a pyrolysis reaction chamber and allowed to react with the coal. This results in higher yields of lighter pyrolysis reaction products including relatively more oils suitable for use as transportation fuels.

The method 100 allows for the closed loop generation of donor hydrogen from earlier generated tail gas. In one embodiment, the method may be considered as a way to recycle hydrogen from the low value tail gas to create lighter pyrolysis reaction products with a relatively higher commercial value. The tail gas may be recycled in a continuous pyrolysis system or may be recycled as part of a batch system that generates and stores formic acid for later batches of coal. The tail gas may be recycled into the same pyrolysis reaction chamber from which it was generated or a different pyrolysis reaction chamber in the same pyrolysis system or a different system.

Figure 2:
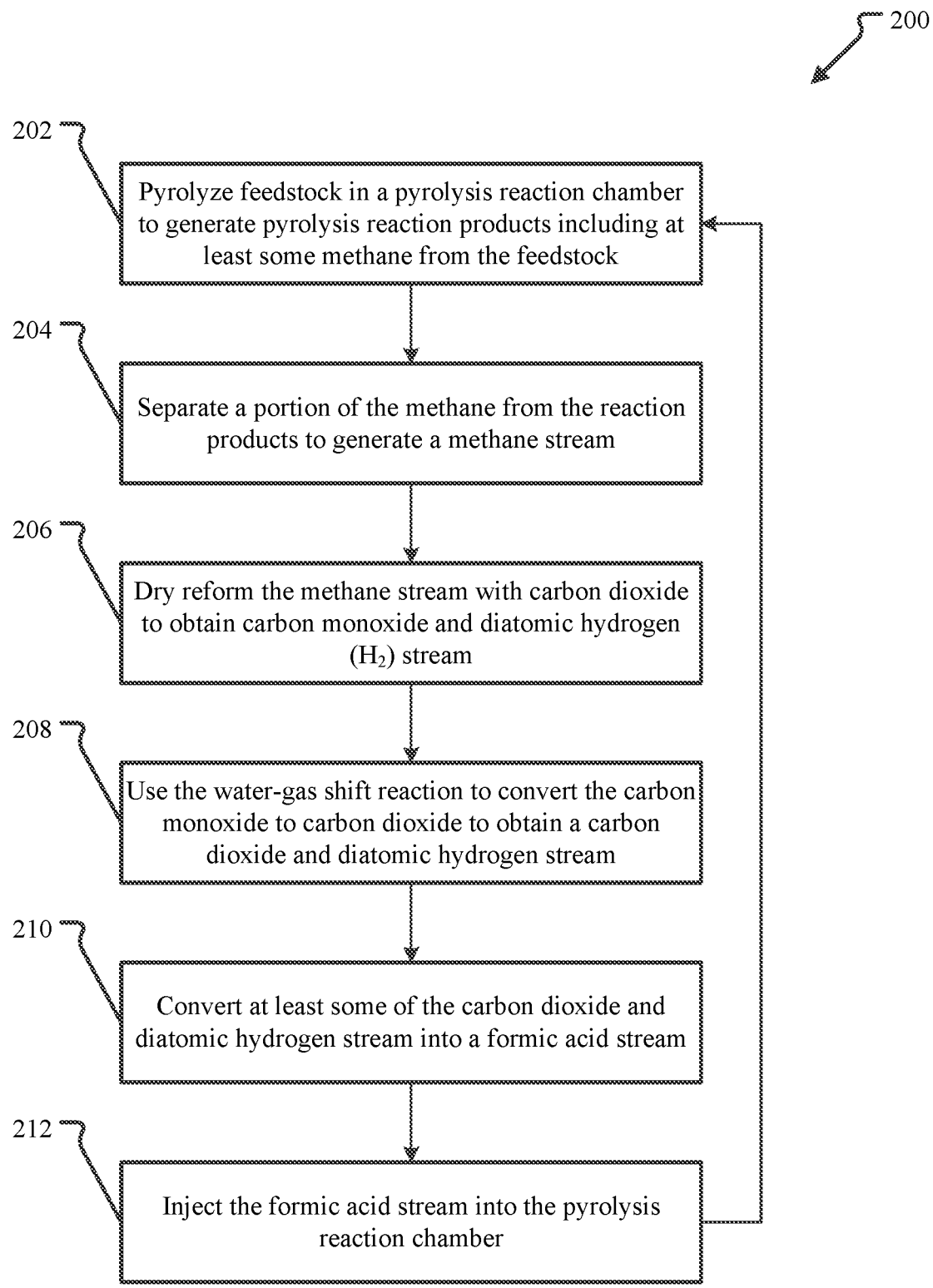
FIG. 2 illustrates a more detailed embodiment of the pyrolysis method of FIG. 1 using coal pyrolyzed in a $sCO_2$ atmosphere.

FIG. 2 illustrates a more detailed embodiment of the pyrolysis method of FIG. 1 using coal pyrolyzed in a sCO$_2$ atmosphere. The method 200 begins with a coal pyrolysis operation 202 in which coal is at least partially pyrolyzed in a pyrolysis reaction chamber in a carbon dioxide atmosphere at a temperature and pressure sufficient to generate at least some reaction products including methane. U.S. Pat. No. 9,376,639, titled METHOD AND SYSTEM FOR PERFORMING GASIFICATION OF CARBONACEOUS FEESTOCK, and U.S. Patent Publication No. 2014/0275668, titled METHOD AND SYSTEM FOR PERFORMING THERMOCHEMICAL CONVERSION OF A CARBONACEOUS FEEDSTOCK TO A REACTION PRODUCT, both of which are incorporated herein by reference, describe methods of pyrolyzing coal, among other feedstocks, to obtain reaction products including methane.

At least some of the methane generated by the pyrolysis operation 202 is then separated from the reaction products and remaining feedstock in a separation operation 204. In an embodiment, this operation 204 includes removing at least some of the sCO$_2$ from the pyrolysis chamber and lowering the temperature and pressure of the sCO$_2$. For example, the sCO$_2$ may be transferred to a separation vessel and the temperature and pressure reduced to room temperature (e.g. 18-22° C.) and one atmosphere (1±20% atm). This results in gaseous CO$_2$ combined with gaseous methane and any of the other compounds generated by the pyrolysis operation 202 that are a gas at those conditions.

In an embodiment, the separation operation 204 includes further separating the ethane and higher (C$_{2+}$) components of tail gas from the methane and CO$_2$ to obtain a CO$_2$ and methane stream. This may be done using any conventional method, now known or later developed, such as, for example, membrane separation using silicone hollow fiber membranes or spiral wound membranes, or using an absorption column as described in U.S. Patent Publication No. 2010/0024647. Other methods are known and any suitable method may be used.

One benefit of generating a CO$_2$ and methane stream with very little or no other compounds of tail gas or reaction products is that it improves the performance of the later chemical operations that ultimately create the formic acid. For example, the subsequent chemical operations (e.g., dry reforming, water shift reaction, and formic acid generation) may include one or more catalyzed reactions. Using a more pure the CO$_2$ and methane stream should improve the performance of the catalysts and reduce the fouling observed, thus improving the economics of the overall system.

That said, the CO$_2$ and methane stream is then passed to a reformer and dry reformed to generate a syngas (H$_2$ and CO) stream in a dry reforming operation 206. The dry reforming reaction may be represented by:

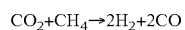

$$CO_2+CH_4 \rightarrow 2H_2+2CO$$

Again, dry reforming, also known as carbon dioxide reforming, is known in the art and any suitable method and reforming system, now known or later developed, may be used. For example, catalytic methods for dry reforming include using noble metals, Ni or Ni alloys. Activated carbon has also been reported as a suitable catalyst.

Regardless of the dry reforming method used, the dry reforming operation 206 generates a syngas stream of substantially pure hydrogen and carbon monoxide. The word 'substantially' is used in recognition that absolutely pure streams of anything are difficult if not impossible to generate. In that sense, for the purposes of this application substantially pure shall mean greater than 90% by mass. Depending on the purity of the stream required, additional filtration and separation steps may be performed to reduce as much as practicable any unreacted methane or errant higher carbon components of tail gas in the syngas stream.

In an embodiment, additional methane may be provided to the $CO_2$ and methane stream if additional hydrogen for the pyrolysis reaction is determined to be needed or beneficial. However, in an embodiment, all additional donor hydrogen ultimately injected into the pyrolysis chamber is generated from methane recovered from the pyrolysis reaction.

The syngas stream is then passed to a water-gas shift reactor or system and converted into $CO_2$ and $H_2$ in a water-gas shift reaction (WGSR) operation 208. In the WGSR operation 208, additional high temperature water or steam may be added to the syngas stream (prior to entering the reactor or to the reactor) under conditions that convert the CO to $CO_2$. The WGSR may be represented by:

$$CO+H_2O \leftrightharpoons CO_2+H_2$$

It should be noted that the syngas stream input into the water-gas shift reactor or system may include significant amounts of water already, as well as trace amounts of tail gas. For example, this may occur if the $CO_2$ is in the supercritical state because the $sCO_2$ will have some $H_2O$ dissolved in it. The dissolved $H_2O$ may be from pyrolysis reaction and was originally in the form of residual moisture in the feedstock. In an embodiment, the amount of water in the syngas stream input into the water-gas shift reactor may be monitored and the amount of water to be added is determined and delivered so that the correct stoichiometric amount water is available for the WGSR. Thus, in this embodiment, a portion of the water entering the water-gas shift reactor is originally from the feedstock and the balance is added as water or steam. Depending on the water content of the feedstock, the amount of additional, or makeup, water provided to the water-gas shift reactor may be varied to convert the converted CO to $CO_2$.

Again, the WGSR is known in the art and any suitable method and reforming system, now known or later developed, may be used. For example, in typical industrial scale applications, WGSR is performed using multiple adiabatic stages including a high temperature stage and low temperature stage, each using a different catalyst (e.g., CuO and $Fe_2O_3$) to improve the reaction yield. As mentioned above, by using substantially pure syngas, the performance of the catalyzed reactions are improved.

Regardless of the WGSR systems and methods used, the WGSR operation 208 generates a stream of substantially pure hydrogen and carbon dioxide. Again, additional filtering or separation processes may be performed to reduce or eliminate any errant CO or other impurities from the stream.

The $CO_2$ and $H_2$ stream is then converted into formic acid in a formic acid generation operation 210. In an embodiment of this operation 210, the $CO_2$ and $H_2$ stream is passed to a formic acid generation system which may include passing the stream through a column containing a catalyst, such as Ru and Ir. The formic acid generation operation 210 may be represented by:

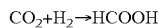

$$CO_2+H_2 \rightarrow HCOOH$$

Again, as mentioned above with reference to FIG. 1, formic acid generation by the direct hydrogenation of $CO_2$ is known in the art and any suitable method and reforming system, now known or later developed, may be used (See, for example, Jessop P G, Hsiao Y, Ikariya T, Noyori R: Homogeneous Catalysis in Supercritical Fluids: Hydrogenation of Supercritical Carbon dioxide to form formic acid, alkyl formats, and formamides. J. Am. Chem. Soc. 1996, 118, 344-355), which is hereby incorporated herein by reference. Regardless of the formic acid generation systems and methods used, the formic acid generation operation 210 is designed to generate a stream of substantially pure formic acid or formic acid and carbon dioxide stream.

The output stream is then input as a feed into a pyrolysis reaction chamber in an injection operation 212. The injection operation 212 may include injecting the formic acid into the same reaction chamber that generated the initial methane from which it was ultimately produced, or a different reaction chamber.

In the method 200, some or all of the dry reforming operation 206, WGSR operation 208, formic acid generation operation 210 may be performed under conditions where the $CO_2$ is changed to or maintained in a supercritical state. This may be especially beneficial in embodiments in which the pyrolysis is done using $sCO_2$.

The method 200 described above was described in terms of a continuous process that generates various streams at different points in the method. In an alternative embodiment the method may be performed as a batch or semi-continuous process in which one or more of the operations are batch operations. For example, in one batch embodiment, every operation is a batch operation that ultimately generates formic acid from a first batch pyrolysis operation 202 for use in a second, later batch pyrolysis operation 202. Additional formic acid may be used in the first pyrolysis operation or that operation may be performed without the benefit of the additional donor hydrogen.

Figure 3:
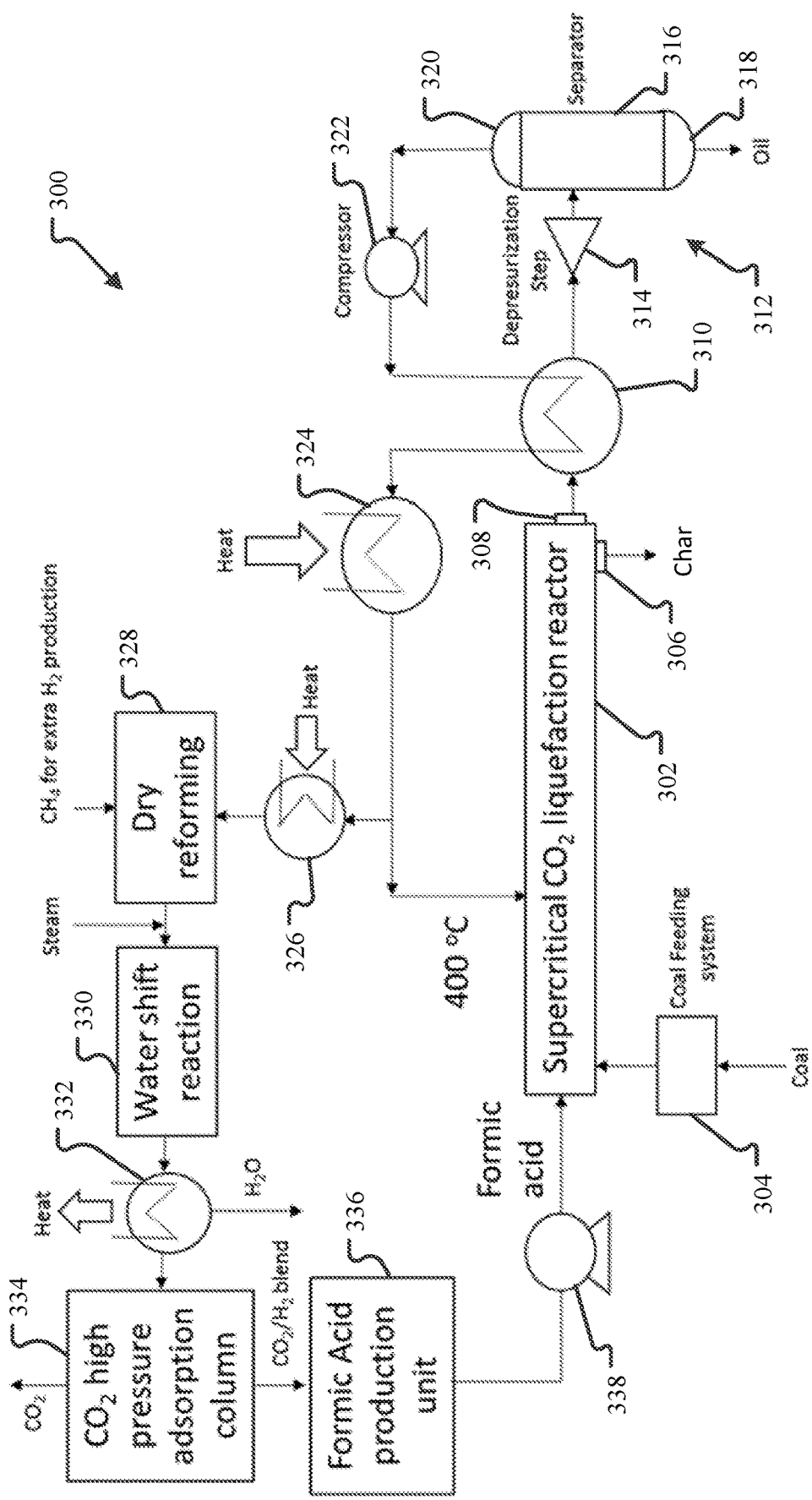
FIG. 3 is an example of a pyrolysis system that implements an embodiment of the formic acid generation methods described above.

FIG. 3 is an example of a pyrolysis system 300 that implements an embodiment of the formic acid generation methods described above. FIG. 3 illustrates a block diagram view of a system 300 for converting carbonaceous material to one or more reaction products. In one embodiment, the system 300 includes a thermochemical conversion system in the form of a $sCO_2$ liquefaction reactor 302. The $sCO_2$ liquefaction reactor 302 is suitable for containing a volume of feedstock material (e.g., carbonaceous material) and converting the feedstock material to one or more reaction products including methane. In the embodiment shown, $sCO_2$ is used to pyrolyze the feedstock, in this case coal, in the $sCO_2$ liquefaction reactor.

Coal is fed into the reactor 302 by a coal feeding system 304. Pyrolyzed coal, primarily in the form of char, is removed from a char outlet 306 in the $sCO_2$ liquefaction reactor 302 and transferred to a char handling system (not shown).

Reaction products of the pyrolysis of the coal are carried in the $sCO_2$ and removed at a xsCO2 outlet 308 in the $sCO_2$ liquefaction reactor 302. The $sCO_2$ is at least partially cooled by a heat exchanger 310 and passes to a separation system 312 that separates pyrolysis reaction products from the $sCO_2$. In the embodiment shown, the separation system 312 includes a depressurization unit such as a nozzle 314 through which the $CO_2$ and pyrolysis products are passed before flowing to a separation unit, such as a column 316. In the column 316, heavier components of the reaction products condense out of the $sCO_2$ and are removed at a liquids outlet 318. Tail gas and $CO_2$ is removed at a gas outlet 320 in the separation unit. Although drawn as a single nozzle 314 and column 316, the separation system 312 may include additional separation stages so that the final gas in the gas outlet stream is controlled to include only methane and $CO_2$.

Regardless of whether the outlet gas is a $CO_2$ and methane mixture, a mixture of $CO_2$ and one or more other separated tail gas components, or a $CO_2$ and tail gas mixture, in the embodiment shown the gas output by the separation system 312 is compressed by a compressor 322 and then preheated by the heat exchanger 310 to recover some of the thermal energy from the output of the reactor 302 as shown. The output gas may then be heated further with heat from a heat source by passing it through one or more additional heaters or heat exchangers 324. In an embodiment, the $CO_2$ is returned to a supercritical state at this point.

As shown in FIG. 3, some of the separation system's outlet gas is directed back into the $sCO_2$ liquefaction reactor and some of the gas is directed to the reformer 328. The reforming system 328 is optional. Additional heat may be added, as shown, to the stream directed to the dry reformer via an intermediate heat exchanger 326. Additional methane may also be added to the dry reformer 328 in the event that additional hydrogen in excess of that in the outlet stream is needed in the pyrolysis reaction. The dry reformer 328 converts the tail gas into syngas and outputs a syngas stream in excess $CO_2$. As discussed above, the syngas stream may include some water and some unreacted tail gas depending on the feedstock.

In an alternative embodiment, not shown, instead of a dry reformer 328 a steam reformer 328 may be used. In this embodiment, water could be added, as necessary, to the stream directed to the steam reformer 328. In an embodiment, the reformation may be achieved through a combination of dry and steam reforming as those reactions may occur in tandem at certain temperature and pressure conditions.

Steam is then added to the syngas stream and passed to a WGSR system 330. The output of the WGSR system 330 is a carbon dioxide and hydrogen stream. This stream is then cooled and any condensed water is removed by a cooling heat exchanger/condenser 332.

The cooled carbon dioxide and hydrogen stream is then passed to a $CO_2$ high pressure adsorption column 334 to remove excess $CO_2$ in anticipation of the formic acid generation reaction. This column outputs a stream including the stoichiometric balance of $CO_2$ and $H_2$. That stream is then passed to the formic acid production unit 336.

In the formic acid production unit 336, the balanced carbon dioxide and hydrogen stream is converted to formic acid which is then pumped back into the $sCO_2$ liquefaction reactor 302. In the embodiment shown, a pump 338 is provided for that purpose.

It is noted herein that the supercritical $CO_2$ may have low viscosity and surface tension allowing it to readily penetrate organic materials (e.g., coal). The penetration of the supercritical fluid into the feedstock reduces the need for converting the feedstock into fine particles prior to thermochemical reaction, thereby saving energy in the reaction of the feedstock material. In one embodiment, the supercritical fluid may be pressurized to above its critical pressure (7.39 MPa) and critical temperature (31° C.). It is noted herein that above these conditions, $CO_2$ will display unique solvency properties, similar to organic solvents such as hexane, methanol and ethanol. The non-polar nature of supercritical $CO_2$ may facilitate the control of undesirable ionic secondary reactions that commonly occur in aqueous environments. Further, $CO_2$ will volatize when the system is depressurized below the critical conditions, which facilitates the recovery of oil with low content of water. Again, this may significantly reduce energy consumption during reaction product-supercritical fluid separation, described further herein, following pyrolysis. It is further noted herein that the supercritical fluid of system 300 applies heated and pressurized $CO_2$ to the feedstock material, which provides for better control of reaction conditions (e.g., time, pressure, and temperature), thereby allowing for better selectivity of high-value targeted chemical compounds or fuel intermediates.

In another embodiment, a supercritical fluid, such as supercritical $CO_2$, may provide strong temperature and reaction time control via the injection of cooler supercritical fluid into the $sCO_2$ liquefaction reactor to quench the reaction or hotter supercritical fluid to accelerate the reaction. It is further recognized that since a number of supercritical fluids, such as supercritical $CO_2$, can be efficiently compressed, pressure conditions within the $sCO_2$ liquefaction reactor may also be used to control thermochemical reactions within the reactor.

In another embodiment, the solubility of one or more reaction products, such as pitch, in the supercritical fluid may be controlled by adding or removing a polar material into the supercritical fluid. For example, the solubility of one or more oils in supercritical carbon dioxide may be controlled by the addition/removal of one or more materials including a polar molecule, such as, but not limited to, $H_2$, $H_2O$, an alcohol and the like. By way of another example, in the case where the feedstock material includes coal, the solubility of one or more oils in $sCO_2$ may be controlled by adding or removing one or more materials including a hydrogen donor molecule, such as, but is not limited to, $H_2$, $H_2O$ and any other hydrogen donor solvents known in the art.

Any type of heat source such as a power plant may be used. In one embodiment, the one or more heat sources include a non-$CO_2$ emitting heat source. In one embodiment, the one or more heat sources include one or more nuclear reactors, solar energy power plants, and hydroelectric power plants. For example, the one or more heat sources may include any nuclear reactor known in the art such as a liquid metal cooled nuclear reactor, a molten salt cooled nuclear reactor, a high temperature water cooled nuclear reactor, a gas cooled nuclear reactor and the like. By way of another example, the one or more heat sources may include a pool reactor. By way of another example, the one or more heat sources may include a modular reactor.

It is recognized herein that a heat source such as a nuclear reactor may generate temperatures sufficient to carry out pyrolysis (e.g., fast pyrolysis) of coal. For example, a nuclear reactor heat source may generate temperatures in excess of 350-600° C. In this regard, the heat source may be used to transfer thermal energy (e.g., at a temperature in excess of 350-600° C.) to the supercritical fluid. In turn, the supercritical fluid may transfer the generated thermal energy to the coal contained within the $sCO_2$ liquefaction reactor.

It is further noted herein that a nuclear reactor heat source may be particularly advantageous as a heat source in the context of this system because the thermochemical reaction temperatures of this system are within the range of operating temperatures for many nuclear reactors. Nuclear reactor heat may be used to create reaction products (e.g., bio-oil) in a $sCO_2$ liquefaction reactor at high efficiency since the nuclear reactor is operating at the reaction temperature for the thermochemical conversion (i.e., heat added at the thermochemical reaction temperature supplies the required reaction enthalpy).

In one embodiment, as shown in FIG. 3, the heat exchangers includes a direct heat exchange system configured to transfer thermal energy directly from the one or more heat sources to the volume of the $sCO_2$ stream or other streams in the system 300. For example, the heat exchangers may be placed in direct thermal communication with a portion of the one or more heat sources. For instance, in the case where the one or more heat sources include a nuclear reactor, one or more coolant systems of the nuclear reactor may be integrated with the thermal energy transfer system. In this regard, the nuclear reactor may utilize a supercritical fluid in one or more coolant systems, which may then be coupled directly to the $sCO_2$ liquefaction reactor. For example, a primary or intermediate coolant loop of the nuclear reactor may include a coolant fluid consisting of a supercritical fluid, such as supercritical $CO_2$.

In an alternative embodiment (not shown), the coolant loop of the nuclear reactor may be directly coupled to the $sCO_2$ liquefaction reactor via the thermal energy transfer system so as to intermix the supercritical fluid of the coolant loop of the nuclear reactor with the feedstock material contained within the $sCO_2$ liquefaction reactor. In turn, upon transferring thermal energy from the nuclear reactor to the feedstock material, the thermal energy transfer system may circulate the supercritical fluid coolant back to the nuclear reactor via a return path. It is further contemplated herein that the thermal energy transfer system may include any number of filtration elements in order to avoid transfer of feedstock and/or reaction products to the coolant system(s) of the nuclear reactor.

In an embodiment, the intermediate heat transfer element may include an intermediate heat transfer loop and one or more heat exchangers. The intermediate heat transfer loop may include any working fluid known in the art suitable for transferring thermal energy. For example, the working fluid of the intermediate heat transfer loop may include, but is not limited to, a liquid salt, a liquid metal, a gas, a supercritical fluid (e.g., supercritical $CO_2$), or water.

It is noted herein that the above description of the direct and indirect coupling between the one or more heat sources and the $sCO_2$ stream and other streams is not limiting and is provided merely for illustrative purposes. It is recognized herein that in a general sense the integration between the one or more heat sources and the $sCO_2$ liquefaction reactor may occur by transferring heat from a primary, intermediate, or ternary heat transfer system (e.g., coolant system) of the one or more heat sources to the working fluid, such as supercritical $CO_2$, of the thermochemical conversion system. It is further recognized herein that this integration may be carried out using any heat transfer systems or devices known in the art, such as, but not limited to, one or more heat transfer circuits, one or more heat sinks, one or more heat exchangers and the like.

In one embodiment, the thermal energy transfer system includes a flow control system (not shown). The flow control system may be arranged to selectably place the supercritical fluid in thermal communication with the coal contained within the $sCO_2$ liquefaction reactor. In this regard, the flow control system may selectably transfer thermal energy from the one or more heat sources to the coal contained within $sCO_2$ liquefaction reactor. For example, the flow control system may be positioned along the piping in order to control the flow of supercritical fluid through the system 300. In this regard, the flow control system may control the flow of the supercritical fluid to the coal, thereby controlling the transfer of thermal energy to the coal.

The flow control system may include any flow control system known in the art suitable for controlling supercritical fluid flow from a first position to a second position. For example, the flow control system may include, but is not limited to, to one or more control valves operably coupled to components in the system 300 and suitable for establishing, stopping and modulating flow through the system 300. For instance, the flow control system may include a manually controlled valve, a valve/valve actuator and the like that control the flow of carbon dioxide from the supercritical $CO_2$ liquefaction reactor 302 to the separation system 312. Likewise, valves may be provided to the control the flow from the intermediate heat exchanger 324 into each of the supercritical $CO_2$ liquefaction reactor 302 and the dry reformer 328.

In one embodiment, the system 300 includes a coal supply system 304. In one embodiment, the coal supply system 304 is operably coupled to the $sCO_2$ liquefaction reactor 302 of the thermochemical conversion system. In another embodiment, the coal supply system 304 provides a volume of coal to the interior of the $sCO_2$ liquefaction reactor 302. The coal supply system 304 may include any supply system known in the art suitable for transferring a selected amount of feedstock material, such as solid material, particulate material or liquid material, from one or more feedstock sources to the interior of the $sCO_2$ liquefaction reactor 302. For example, the coal supply system 304 may include, but is not limited to, a conveyor system, a fluid transfer system and the like.

The coal supply system 304 may include separate systems for transferring the feedstock and transferring additional water in the amount necessary for the desired reaction. In an alternative embodiment, water may be added to the feedstock prior to the transfer of the coal into the $sCO_2$ liquefaction reactor 302. This may be done in the coal supply system 304 or prior to receipt by the coal supply system.

A moisture control system (not shown) may be provided to determine the moisture of the coal and to add water if necessary. Water addition, for example, may be further controlled based on the amount of water needed for the WSGR. Such a system may include a moisture detector that continuously or periodically determines the moisture of the coal, compares the moisture to a target water content range and adds water if the moisture is below the target range. A dryer may also be provided in case the moisture is above the target range for drying the coal.

It is noted herein that the ability to control temperature, pressure, reaction time, pre-treatment options, and post organic-product production options may allow for multiple types of carbonaceous feedstock to be utilized within the system 300. In addition, the ability to co-utilize or switch between types of feedstock may improve the utilization of available resources and improve the overall pitch production economics.

Referring again to FIG. 3, the thermochemical conversion system includes any $sCO_2$ liquefaction reactor 302 suitable for carrying out pyrolysis. In one embodiment, the $sCO_2$ liquefaction reactor is configured to carry out a pyrolysis reaction on the coal. In another embodiment, the $sCO_2$ liquefaction reactor includes a pyrolysis chamber. In another embodiment, the $sCO_2$ liquefaction reactor includes a non-combustion or low-combustion pyrolysis chamber. The $sCO_2$ liquefaction reactor of system 300 may encompass any thermochemical reaction chamber suitable for carrying out the thermochemical decomposition of organic molecules in the absence of oxygen or in a low oxygen environment.

In one embodiment, the $sCO_2$ liquefaction reactor 302 includes a fast pyrolysis reactor suitable for converting feedstock, such as coal, to reaction products including pitch, bio-oil, methane and other hydrocarbons. A fast pyrolysis reactor may include any thermochemical reaction chamber capable of carrying out a thermochemical decomposition of organic molecules in the absence of oxygen (or in a reduced oxygen environment) within approximately two seconds. Fast pyrolysis is generally described by Roel J. M. Westerhof et al. in "Effect of Temperature in Fluidized Bed Fast Pyrolysis of Biomass: Oil Quality Assessment in Test Units," Industrial & Engineering Chemistry Research, Volume 49 Issue 3 (2010), pp. 1160-1168, which is incorporated herein by reference in the entirety. Pyrolysis and fast pyrolysis are also generally described by Ayhan Demirbas et al. in "An Overview of Biomass Pyrolysis," Energy Sources, Volume 24 Issue 3 (2002), pp. 471-482, which is incorporated herein by reference in the entirety.

In another embodiment, the $sCO_2$ liquefaction reactor includes a supercritical pyrolysis reactor suitable for converting feedstock, such as coal or biomass, to a reaction product. For the purposes of the present disclosure, a 'supercritical $CO_2$ liquefaction reactor' and a 'pyrolysis reactor' are interpreted to encompass any reactor, reaction vessel, or reaction chamber suitable for carrying out a pyrolysis reaction of feedstock material using the thermal energy supplied from a supercritical fluid. In another embodiment, the $sCO_2$ liquefaction reactor may include, but is not limited to, a fluidized bed reactor.

In another embodiment, the $sCO_2$ liquefaction reactor may carry out one or more extraction processes on the feedstock. In one embodiment, the $sCO_2$ liquefaction reactor is configured to remove additional compounds from the feedstock material prior to pyrolysis. For example, the $sCO_2$ liquefaction reactor may be configured to remove at least one of oils and lipids, sugars, or other oxygenated compounds. In another embodiment, the extracted compounds may be collected and stored for the development of additional bio-derived products.

It may be advantageous to remove sugars from the feedstock materials other than coal. It is recognized herein that sugars caramelize at elevated temperature and may act to block the supercritical fluid, such as supercritical $CO_2$, from entering the cellulose structure of the feedstock material. In addition, sugars present in the thermochemical conversion system may also act to harm downstream catalyst beds (if any). It is noted herein that the removal of sugars aids in avoiding the formation of oxygenated compounds such as, but not limited to, furfural, hydroxymethalfurfural, vanillin and the like.

In one embodiment, the thermochemical conversion system may extract materials from the coal at temperatures below 200° C. It is noted herein that it is beneficial to extract sugars at temperatures below 200° C. as fructose, sucrose and maltose each caramelize at temperatures below approximately 180° C. In this regard, the supercritical fluid, through the deconstruction of cellulosic material and the sweeping away of sugars, may serve to extract sugars from the feedstock prior to the elevation of temperatures during pyrolysis.

In another embodiment, the $sCO_2$ liquefaction reactor is configured to pre-heat the feedstock prior to thermal decomposition. In another embodiment, a pre-heating chamber operably coupled to the $sCO_2$ liquefaction reactor is configured to pre-heat the feedstock prior to thermal decomposition. For example, the $sCO_2$ liquefaction reactor (or the pre-heating chamber) may pre-heat the feedstock material to a temperature at or near the temperature necessary for liquefaction and/or pyrolysis.

In another embodiment, the $sCO_2$ liquefaction reactor is configured to pre-treat the coal prior to thermal decomposition. For example, the $sCO_2$ liquefaction reactor may pre-hydrotreat the coal with hydrogen prior to liquefaction and/or pyrolysis. For instance, pre-treating the coal with hydrogen may aid in removing materials such as, but not limited to, sulfur, as well as serving to donate hydrogen to broken dangling bonds (i.e., stabilizing free radicals).

In an alternative embodiment, not shown, the $sCO_2$ liquefaction reactor is separated into multiple process chambers for carrying out the various steps of the multi-stage thermochemical process of the system. For example, in one embodiment, a first chamber is provided for the first stage of pyrolysis, a second stage is provided for the second stage of pyrolysis, and an extraction chamber is provided for solvent contacting and for extracting the solvent with the desired reaction products. The coal may be transferred between the chambers continuously or as a batch process.

Applicants note that while the above description points out that in some embodiments the pyrolysis reaction chambers and extraction chamber may exist as separate chambers, this should not be interpreted as a limitation. Rather, it is contemplated herein that two or more of the thermochemical steps may each be carried out in a single reaction chamber.

In one embodiment, the $sCO_2$ liquefaction reactor includes a multi-stage single thermochemical reaction chamber. In one embodiment, the $sCO_2$ liquefaction reactor is configured to transfer multiple portions of the supercritical fluid across multiple temperature ranges to the volume of coal contained within the multi-stage single $sCO_2$ liquefaction reactor to perform a set of thermochemical reaction processes on at least a portion of the volume of feedstock.

In one embodiment, the flow and temperature of the supercritical fluid are varied spatially across the $sCO_2$ liquefaction reactor. For example, in order to vary flow and/or temperature across the $sCO_2$ liquefaction reactor, multiple flows of supercritical fluid, each at a different temperature, may be established prior to entering the single reaction chamber. In this regard, in a vertical reaction chamber, the flow rate and temperature at a number of spatial locations, corresponding to the various thermochemical stages, may be varied. By way of another example, the temperature of the supercritical fluid may be varied along the length of the $sCO_2$ liquefaction reactor by flowing the supercritical fluid along the length of the $sCO_2$ liquefaction reactor. For instance, a flow of low temperature supercritical $CO_2$ may be combined with a flow of $CO_2$ at a higher temperature (e.g., between 70 to 150° C.) to dissolve sugars. At another point downstream (e.g., 1-3 meters downstream with an average flow rate of 0.25-4 m/s), supercritical $CO_2$ at or above pyrolysis temperatures is mixed into the chamber. By staging the temperatures of the various thermochemical reaction steps according to length, the flow rate may be used to control reaction times.

It is further contemplated that two or more thermochemical steps, such as pyrolysis, extraction and separation, are carried out in the $sCO_2$ liquefaction reactor, while additional steps, such as drying and pre-heating are carried out in a dedicated chamber operably coupled to the $sCO_2$ liquefaction reactor.

In an embodiment, the char and pyrolysis residue storage system may be as simple as a drum, railcar, Conex box or other portable container. In an alternative embodiment, the residue may be stored in piles for later transport.

Other compounds in the solvent stream removed from the $sCO_2$ liquefaction reactor are collected for further treatment or sale in a product collection system (not shown). In one embodiment, a volatile gas separator and storage system may be provided as part of the product collection system or the separation system 312. The volatile gas separator may separate one or more volatile gases from the remainder of the one or more reaction products. For example, the volatile gas separator may separate volatile gases such as, but not limited to, $CH_4$, $C_2H_4$, $C_2H_6$, CO, $CO_2$, $H_2$, $H_2O$ from the solid or liquid reaction products. It is noted herein that the volatile gas separator may include any volatile gas separation device or process known in the art. It is further recognized that these gases may be cooled, cleaned, collected and stored for future utilization.

In the embodiment shown, the $CO_2$ is reheated and returned to the $sCO_2$ liquefaction reactor 302 after the dissolved products are removed in a closed loop system. In an alternative embodiment the $CO_2$ is simply vented and only fresh $sCO_2$ is provided to the $sCO_2$ liquefaction reactor 302.

In another embodiment, the system 300 includes a heat recovery system. In the case of recovery, the system may recover heat from the $sCO_2$ prior to or as part of the separation unit, as shown, (or any other appropriate subsystem of system 300) via a heat transfer loop acting to thermally couple the $sCO_2$ and the heat recovery system. In one embodiment, the recovered heat may serve as a recuperator or regenerator. In another embodiment, energy may be recovered following the thermochemical process carried out by $sCO_2$ liquefaction reactor. In another embodiment, the recovered energy may be used to pre-heat feedstock material prior to thermochemical processing. In another embodiment, the recovered energy may be used to produce ancillary power (e.g., mechanical power or electrical power) to one or more sub-systems of the system 300.

Figure 4:
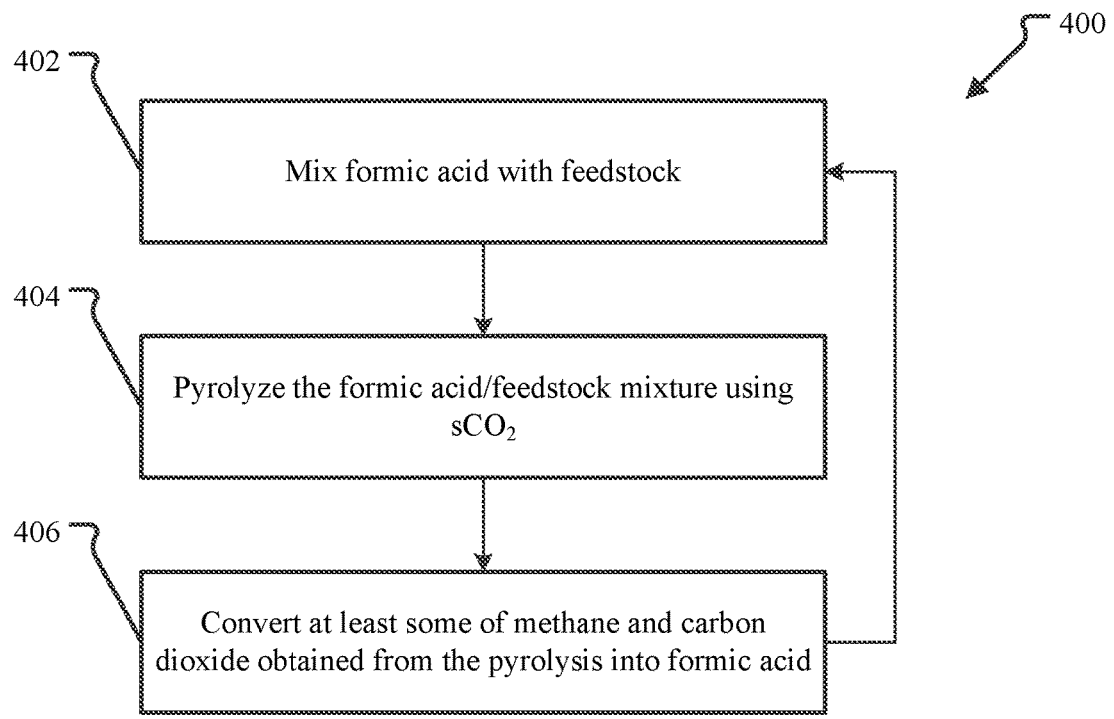
FIG. 4 illustrates an embodiment of another method of pyrolyzing a feedstock such as coal.

FIG. 4 illustrates an embodiment of another method of pyrolyzing a feedstock such as coal. In the embodiment of the method 400 illustrated, formic acid and the feedstock are mixed in a mixing operation 402 prior to pyrolyzing the mixture in a pyrolysis operation 404. In an embodiment, the mixing of the formic acid and the feedstock is performed at a temperature less than 100° C. and a pressure less than 1 MPa. For example, the mixing may be performed at room temperature to obtain slurry of feedstock particles and formic acid. In an alternative embodiment, the mixing is performed at a temperature and pressure at which carbon dioxide is in the supercritical state. The pyrolysis may be performed using supercritical carbon dioxide, for example as described above, at a first temperature from 150-600° C. and a first pressure from 7-12 MPa. After mixing and pyrolyzing the formic acid and feedstock mixture, at least some of the tail gas generated by the pyrolysis is then converted into formic acid in a conversion operation 406 as described above. The formic acid obtained from the conversion operation 406 is then mixed with fresh feedstock for further pyrolysis as shown.

Figure 5:
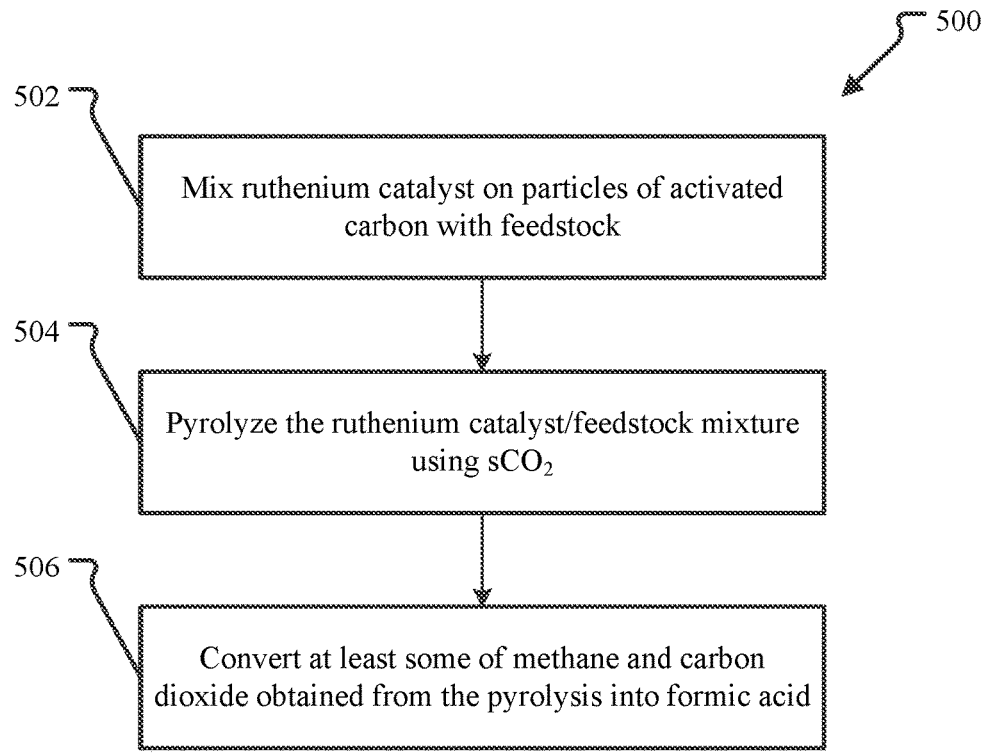
FIG. 5 illustrates an embodiment of yet another method of pyrolyzing a feedstock such as coal using a ruthenium catalyst.

FIG. 5 illustrates yet another embodiment of a method of pyrolyzing a feedstock such as coal. In the embodiment of the method 500 illustrated, one or more ruthenium catalysts are supported on particles of activated carbon to obtain a feedstock and ruthenium catalyst mixture. In this method 500, the particle size of activated carbon may be selected to be similar or less than the particle size of the feedstock. In an embodiment, the particles of activated carbon have a mean particle diameter (mpd) less than 0.045 mm (e.g., passes through a 325US Mesh). Alternatively, the particles of activated carbon may have a mean particle diameter of less than 0.180 mm (e.g., passes through a 80US Mesh), less than 0.5 mm (e.g., passes through a 35US Mesh) or even less than 25.4 mm (e.g., passes through a 1 inch US Mesh). Ruthenium catalysts are well known in the art. The ruthenium catalyst or catalysts used may be any known in the art now or later developed.

The feedstock and ruthenium catalyst/activated carbon particles are mixed in a mixing operation 502 prior to pyrolyzing the mixture in a pyrolysis operation 504. In an embodiment, the mixing of the ruthenium catalyst/activated carbon particles and the feedstock is performed at a temperature less than 100° C. and a pressure less than 1 MPa. For example, the mixing may be performed at room temperature to obtain mixture of feedstock particles and ruthenium catalyst/activated carbon particles. In an alternative embodiment, the mixing is performed at a temperature and pressure at which carbon dioxide is in the supercritical state and in a carbon dioxide environment. The pyrolysis may be performed using supercritical carbon dioxide, for example as described above, at a first temperature from 150-600° C. and a first pressure from 7-12 MPa. After mixing and pyrolyzing the ruthenium catalyst/activated carbon particles and feedstock mixture, at least some of the tail gas generated by the pyrolysis is then converted into formic acid in a conversion operation 506 as described above. The formic acid obtained from the conversion operation 506 may be later used in a further pyrolysis operation.

Figure 6:
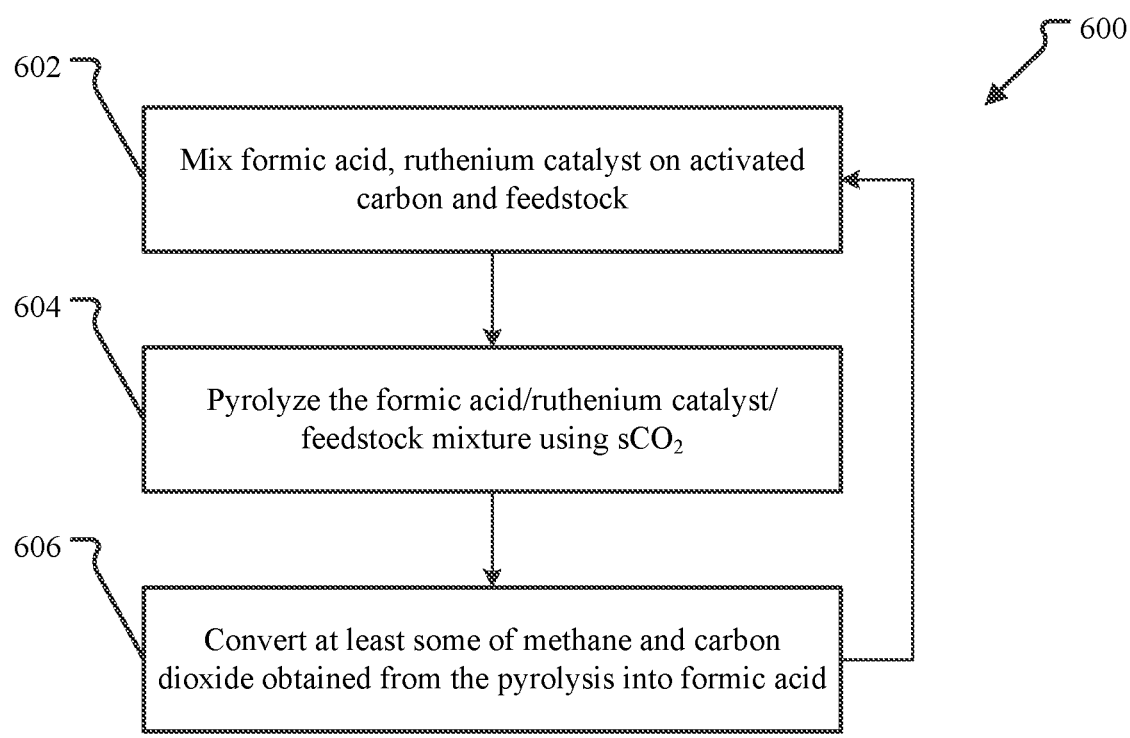
FIG. 6 illustrates an embodiment of yet another method of pyrolyzing a feedstock such as coal using a ruthenium catalyst and formic acid.

FIG. 6 illustrates an embodiment of another method of pyrolyzing a feedstock such as coal. In the embodiment of the method 600 illustrated, formic acid, ruthenium catalyst/activated carbon particles (as described above with reference to FIG. 5) and the feedstock are mixed in a mixing operation 602 prior to pyrolyzing the mixture in a pyrolysis operation 604. In an embodiment, the mixing of the formic acid, ruthenium catalyst/activated carbon particles and the feedstock is performed at a temperature less than 100° C. and a pressure of less than 1 MPa. For example, the mixing may be performed at room temperature to obtain slurry of feedstock particles and ruthenium catalyst/activated carbon particles in formic acid. In an alternative embodiment, the mixing is performed at a temperature and pressure at which carbon dioxide is in the supercritical state. The pyrolysis 604 may be performed using supercritical carbon dioxide, for example as described above, at a first temperature from 150-600° C. and a first pressure from 7-12 MPa. After mixing and pyrolyzing the formic acid/ruthenium catalyst/activated carbon particles/feedstock mixture, at least some of the tail gas generated by the pyrolysis is then converted into formic acid in a conversion operation 606 as described above. The formic acid obtained from the conversion operation 606 is then mixed with fresh feedstock for further pyrolysis as shown.

EXAMPLES

A pyrolysis reactor in the form of a pressurized tube reactor heated by immersion into a hot sand reactor was used to investigate the performance of formic acid as a source of free hydrogen in pyrolysis of coal. Briefly, 1.2 g of coal powder was transferred into a 15 ml tube reactor. Tests were conducted with and without formic acid (FA) (FA:Coal=0:1 and 1:1). After weighing the mass, the closed tube reactor with the samples were then pressurized. A leak check was first conducted by pressurizing the tube reactor to 1,100 psi with $H_2$. The whole system was inspected with a leak detector. The reactor was then flushed three times with $N_2$. Subsequently the reactor was pressurized with 400 psi of $H_2$, $CO_2$ or the combination of both (resulting in 800 psi) to obtain $H_2/CO_2$ ratios of 1:1. The pressurized tube reactor was then transferred into the preheated sand bath for coal liquefaction and pyrolysis. It took 1.5 minutes for the reactor to achieve 450° C. from 25° C. The reactor was then maintained at the temperature of 450° C. for 10 minutes then cooled back to 25° C. After cooling, the reactor was cleaned and pressure inside was released in a hood. The total weight after gas releasing was measured. In the product recovery step, toluene was used to wash the leftover char out of the tube reactor and the usage was recorded. The product slurry then underwent a two phase solxet extraction. The solid residue after extraction was dried and considered to be the char product. The yield of liquid was calculated by the difference between the initial 1.2 g of coal and the weight of the char product.

Table 1 shows the experimental results of the tests with and without formic acid. As can be observed the use of formic acid increased the yield of liquid from 8.2 to 30.3 wt. %. The yield of gases and solids were reduced.

TABLE 1

Yield of products in the presence and absence of formic acid (FA) (wt. %)

|  | FA 0%[1] | FA100%[2] |
| --- | --- | --- |
| Gas | 19.8 | 10.9 |
| Solid | 72.0 | 58.8 |
| Liquid | 8.2 | 30.3 |

[1]FA: Coal = 0:1, 450° C., 10 min, 400 psi $H_2$/400 psi $CO_2$.
[2]FA: Coal = 1:1, 450° C., 10 min, 400 psi $H_2$/400 psi $CO_2$.

A ruthenium catalyst experiment was also performed. An Ru/activated carbon catalyst in the form of activated carbon powder supporting Ru was created from $RuCl_2*xH_2O$ and 100 US Mesh (0.149 mm mean particle size) activated carbon powder from Signa Aldrich. The Ru catalyst was mixed with coal particles of approximately the same size and pyrolyzed under the same conditions as the FA 0% experiment reported above. When the Ru/activated carbon catalyst was blended with coal, a liquid yield higher than 50 wt. % was observed. This is a greater increase in the yield of oil than was observed from results of prior experiments using pure Ru directly added to coal under the same conditions.

Notwithstanding the appended claims, the disclosure is also defined by the following numbered clauses:

1. A method comprising:
pyrolyzing feedstock to generate pyrolysis reaction products including at least some tail gas from the feedstock;
separating a portion of the at least some tail gas and carbon dioxide from the reaction products into separated tail gas, wherein the separated tail gas includes one or more components of the tail gas;
converting at least some of the separated tail gas and carbon dioxide to formic acid; and
injecting at least some of the formic acid into a pyrolysis reaction.

2. The method of clause 1 further comprising:
separating a stream of methane and carbon dioxide from the reaction products; and
converting at least some of the separated methane and carbon dioxide to formic acid.

3. The method of clauses 1 or 2 wherein the pyrolysis is performed using supercritical carbon dioxide at a first temperature from 150-600° C. and a first pressure from 7-12 MPa.

4. The method of clauses 1, 2, or 3 wherein the feedstock is selected from bituminous coal, sub-bituminous coal, lignite, and anthracite.

5. A method of pyrolyzing coal comprising:
pyrolyzing coal in a carbon dioxide atmosphere in a reactor at a temperature and pressure at which the carbon dioxide is in a supercritical state to generate reaction products including at least some methane;
removing at least some of the supercritical carbon dioxide and reaction products from the reactor;
separating at least some methane and carbon dioxide from the removed supercritical carbon dioxide and reaction products to generate a first stream including at least methane and carbon dioxide;
reforming at least a portion of the first stream to generate a second stream including at least hydrogen and carbon monoxide;
converting at least a portion of the second stream into a third stream including hydrogen and carbon dioxide;
converting at least a portion of the third stream into formic acid via a formic acid generation reaction; and
injecting at least some of the generated formic acid into a pyrolysis reaction.

6. The method of clause 5 wherein separating at least some methane and carbon dioxide from the removed supercritical carbon dioxide and reaction products includes lowering the temperature, the pressure, or both of the carbon dioxide.

7. The method of clauses 5 or 6 wherein injecting the generated formic acid includes injecting the formic acid into the reactor.

8. The method of clause 5, 6, or 7 wherein converting at least a portion of the second stream into a third stream including hydrogen and carbon dioxide further comprises:
using the water-gas shift reaction to convert at least a portion of the second stream into a third stream including hydrogen and carbon dioxide; and
wherein at least one of the dry reforming, the water-gas shift reaction, and the formic acid generation reaction is performed at temperatures and pressures for which the carbon dioxide is in the supercritical state.

9. The method of any of clauses 5-8 wherein the dry reforming, the water-gas shift reaction, and the formic acid generation reaction are performed at temperatures and pressures for which the carbon dioxide is in the supercritical state.

10. A system for pyrolyzing coal comprising:
at least one reaction chamber capable of pyrolyzing a coal in a supercritical carbon dioxide atmosphere;
a separation system configured to receive the supercritical carbon dioxide atmosphere from the reaction chamber after pyrolysis of the coal, condense reaction products from the carbon dioxide and generate a tail gas and carbon dioxide stream;
a dry reforming system configured to reform the tail gas and carbon dioxide stream into a first stream containing syngas;
a water-gas shift reactor configured to convert at least some of the first stream into a second stream containing carbon dioxide and hydrogen;
a formic acid production unit configured to convert at least some of the second stream into a third stream containing formic acid; and
an injection system configured to inject the formic acid into the at least one reaction chamber.

11. The system of clause 10 wherein the reaction chamber is capable of heating the coal to a temperature sufficient to generate at least some reaction products including methane.

12. The system of clauses 10 or 11 further comprising:
a heat source that provides thermal energy to the reaction chamber.

13. The system of any of clauses 10-12 further comprising:
a nuclear reactor that provides thermal energy to the reaction chamber.

14. The system of any of clauses 10-13 further comprising:
a heat source that provides thermal energy to the carbon dioxide prior to injecting the carbon dioxide into the reaction chamber.

15. The system of any of clauses 10-14 further comprising:
a nuclear reactor that provides thermal energy to the carbon dioxide prior to injecting the carbon dioxide into the reaction chamber.

16. The system of any of clauses 10-15 wherein the reaction chamber is capable of heating the carbon dioxide to a supercritical state.

17. The system of any of clauses 10-16 further comprising:
a valve that controls the flow of carbon dioxide from the reaction chamber to the separation system.

18. The system of any of clauses 10-17 wherein the separation system includes volatile gas separation system.

19. A system for pyrolyzing coal comprising:
at least one reaction chamber capable of pyrolyzing a coal in a supercritical carbon dioxide atmosphere to form reaction products;
a formic acid generation system configured to convert at least some the reaction products into formic acid; and
an injection system configured to inject the formic acid into the at least one reaction chamber.

20. The system of clause 19 wherein the formic acid generation system comprises:
a separation system configured to receive the supercritical carbon dioxide atmosphere from the reaction chamber after pyrolysis of the coal, condense reaction products from the carbon dioxide and generate a tail gas and carbon dioxide stream;
a dry reforming system configured to reform the tail gas and carbon dioxide stream into a first stream containing syngas;
a water-gas shift reactor configured to convert at least some of the first stream into a second stream containing carbon dioxide and hydrogen; and
a formic acid production unit configured to convert at least some of the second stream into a third stream containing formic acid.

21. The system of clauses 19 or 20 wherein the reaction chamber is capable of heating the coal to a temperature sufficient to generate at least some reaction products including methane.

22. The system of any of clauses 19-21 further comprising:
a heat source that provides thermal energy to the reaction chamber.

23. The system of any of clauses 19-22 further comprising:
a nuclear reactor that provides thermal energy to the reaction chamber.

24. The system of any of clauses 19-23 further comprising:
a heat source that provides thermal energy to the carbon dioxide prior to injecting the carbon dioxide into the reaction chamber.

25. The system of any of clauses 19-24 further comprising:
a nuclear reactor that provides thermal energy to the carbon dioxide prior to injecting the carbon dioxide into the reaction chamber.

26. The system of any of clauses 19-25 wherein the reaction chamber is capable of heating the carbon dioxide to a supercritical state.

27. The system of any of clauses 19-26 further comprising:
a valve that controls the flow of carbon dioxide from the reaction chamber to the separation system.

28. The system of any of clauses 19-21 wherein the separation system includes volatile gas separation system.

29. A method comprising:
providing a first stream containing at least some methane and supercritical carbon dioxide;
converting at least some of the methane and carbon dioxide in the first stream into formic acid; and
injecting at least some of the formic acid into a pyrolysis reaction.

30. The method of clause 29 wherein the first stream is derived from pyrolysis reaction products.

31. The method of clause 30 further comprising:
pyrolyzing feedstock to generate the pyrolysis reaction products.

32. The method of any of clauses 29-31 wherein the first stream includes at least some tail gas from pyrolyzed feedstock.

33. The method of any of clauses 29-32 further comprising:
maintaining the carbon dioxide in the supercritical state during the converting operation.

34. The method of any of clauses 29-33 further comprising:
mixing the formic acid with feedstock to obtain a feedstock and formic acid mixture; and
pyrolyzing the feedstock and formic acid mixture to generate pyrolysis reaction products including at least some tail gas from the feedstock.

35. The method of clause 34, wherein the mixing further comprises:
mixing the formic acid and the feedstock at a temperature less than 100° C. and a pressure less than 1 MPa.

36. The method of any of clauses 29-35 wherein the pyrolysis is performed using supercritical carbon dioxide at a first temperature from 150-600° C. and a first pressure from 7-12 MPa and the feedstock is selected from bituminous coal, sub-bituminous coal, lignite, and anthracite.

37. The method of any of clauses 29-36 further comprising:
mixing the feedstock with a ruthenium catalyst supported on particles of activated carbon to obtain a feedstock and ruthenium catalyst mixture.

38. The method of clause 37 further comprising:
pyrolyzing the feedstock and ruthenium catalyst mixture to generate pyrolysis reaction products including at least some tail gas from the feedstock.

39. The method of any of clauses 29-38 further comprising:
mixing the feedstock with formic acid and a ruthenium catalyst supported on particles of activated carbon to obtain a feedstock/formic acid/ruthenium catalyst mixture.

40. The method of clause 39 further comprising:
pyrolyzing the feedstock/formic acid/ruthenium catalyst mixture to generate pyrolysis reaction products including at least some tail gas from the feedstock.

41. The method of clause 39, wherein the mixing further comprises:
mixing the formic acid, ruthenium catalyst, and the feedstock at a temperature less than 100° C. and a pressure less than 1 MPa to obtain the feedstock/formic acid/ruthenium catalyst mixture.

42. The method of clause 39, wherein the particles of activated carbon have a mean particle diameter (mpd) less than 0.045 mm (e.g., passes through a 325US Mesh).

43. The method of clause 39, wherein the particles of activated carbon have a mean particle diameter of less than 0.180 mm (e.g., passes through a 80US Mesh).

44. The method of clause 39, wherein the particles of activated carbon have a mean particle diameter of less than 0.5 mm (e.g., passes through a 35US Mesh).

45. The method of clause 39, wherein the particles of activated carbon have a mean particle diameter of less than 25.4 mm (e.g., passes through a 1 inch US Mesh).

It will be clear that the systems and methods described herein are well adapted to attain the ends and advantages mentioned as well as those inherent therein. Those skilled in the art will recognize that the methods and systems within this specification may be implemented in many manners and as such are not to be limited by the foregoing exemplified embodiments and examples. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope contemplated by the present disclosure. For example, in an embodiment, the atmosphere of the pyrolysis methods may be different than the $sCO_2$ atmosphere described above while still using $sCO_2$ as the solvent in the extraction and formic acid generation/hydrogen recovery operations of the methods. In this embodiment, the pyrolysis atmosphere may be removed and replaced with $sCO_2$ as part of an extraction operation. Numerous other changes may be made which will readily suggest themselves to those skilled in the art and which are encompassed in the spirit of the disclosure.

What is claimed is:

1. A method comprising:
providing a first stream containing at least some methane and supercritical carbon dioxide;
converting at least some of the methane and the supercritical carbon dioxide in the first stream into formic acid; and
injecting at least some of the formic acid into a pyrolysis reaction.

2. The method of claim 1 wherein the first stream is derived from pyrolysis reaction products.

3. The method of claim 2 further comprising:
pyrolyzing a feedstock to generate the pyrolysis reaction products.

4. The method of claim 1 wherein the first stream includes at least some tail gas from a pyrolyzed feedstock.

5. The method of claim 1 further comprising:
maintaining the carbon dioxide in the supercritical state during the converting operation.

6. The method of claim 3 further comprising:
mixing the formic acid with the feedstock to obtain a feedstock and formic acid mixture; and
pyrolyzing the feedstock and formic acid mixture to generate pyrolysis reaction products including at least some tail gas.

7. The method of claim 6, wherein the mixing further comprises:
mixing the formic acid and the feedstock at a temperature less than 100 ° C. and a pressure less than 1 MPa.

8. The method of claim 3 wherein the pyrolyzing is performed using supercritical carbon dioxide at a first temperature from 150-600 ° C. and a first pressure from 7-12 MPa and the feedstock is selected from bituminous coal, sub-bituminous coal, lignite, and anthracite.

9. The method of claim 3 further comprising:
mixing the feedstock with a ruthenium catalyst supported on particles of activated carbon to obtain a feedstock and ruthenium catalyst mixture; and
pyrolyzing the feedstock and ruthenium catalyst mixture to generate pyrolysis reaction products including at least some tail gas.

10. The method of claim 2 further comprising:
mixing a feedstock with formic acid and a ruthenium catalyst supported on particles of activated carbon to obtain a feedstock/formic acid/ruthenium catalyst mixture; and
pyrolyzing the feedstock/formic acid/ruthenium catalyst mixture to generate pyrolysis reaction products including at least some tail gas.

11. The method of claim 9, wherein the particles of activated carbon have a mean particle diameter of less than 25.4 mm measured by passing through a 1 inch US Mesh.

12. A method comprising:
pyrolyzing a feedstock to generate an output stream containing carbon dioxide and pyrolysis reaction products, the pyrolysis reaction products including at least some tail gas;
converting at least some of the tail gas and carbon dioxide from the output stream to formic acid;
injecting at least some of the formic acid into the step of pyrolyzing the feedstock.

13. The method of claim 12 further comprising:
separating a portion of the at least some tail gas and carbon dioxide from the output stream containing carbon dioxide and pyrolysis reaction products.

14. The method of claim 12 further comprising:
separating a stream of methane and carbon dioxide from the output stream containing carbon dioxide and pyrolysis reaction products; and
converting at least some of the separated methane and carbon dioxide to formic acid.

15. The method of claim 12 wherein the pyrolyzing is performed using supercritical carbon dioxide at a first temperature from 150-600 ° C. and a first pressure from 7-12 MPa.

16. The method of claim 13 wherein the feedstock is selected from bituminous coal, sub-bituminous coal, lignite, and anthracite.

17. A method of pyrolyzing coal comprising:
pyrolyzing a first feedstock comprising coal in a carbon dioxide atmosphere in a reactor at a temperature and pressure at which the carbon dioxide is in a supercritical state to generate reaction products including at least some methane;
removing at least some of the supercritical carbon dioxide and reaction products from the reactor;

separating at least some methane and carbon dioxide from the removed supercritical carbon dioxide and reaction products to generate a first stream including at least methane and carbon dioxide;

dry reforming at least a portion of the first stream to generate a second stream including at least hydrogen and carbon monoxide;

converting at least a portion of the second stream into a third stream including hydrogen and carbon dioxide using the water-gas shift reaction;

converting at least a portion of the third stream into formic acid via a formic acid generation reaction; and combining at least some of the generated formic acid with the first feedstock prior to or during pyrolysis of the first feedstock, or combining at least some of the generated formic acid with a second feedstock of a separate, different pyrolysis reactor.

* * * * *